(12) United States Patent
Kawakami

(10) Patent No.: US 6,713,632 B1
(45) Date of Patent: Mar. 30, 2004

(54) PROCESS FOR THE PREPARATION OF IMIDAZOLE DERIVATIVES

(75) Inventor: Jun-ichi Kawakami, Ikoma (JP)

(73) Assignee: Takeda Chemical Industries, Ltd., Osaka (JP)

(*) Notice: Subject to any disclaimer, the term of this patent is extended or adjusted under 35 U.S.C. 154(b) by 0 days.

(21) Appl. No.: 10/019,094

(22) PCT Filed: Jun. 21, 2000

(86) PCT No.: PCT/JP00/04036
§ 371 (c)(1),
(2), (4) Date: Apr. 12, 2002

(87) PCT Pub. No.: WO00/78727
PCT Pub. Date: Dec. 28, 2000

(30) Foreign Application Priority Data

Jun. 22, 1999 (JP) ............................................ 11/175070

(51) Int. Cl.7 ............................................. C07P 233/54
(52) U.S. Cl. ................................ 548/335.1; 548/341.5; 546/274.7
(58) Field of Search ............................ 548/334.1, 341.5

(56) References Cited

U.S. PATENT DOCUMENTS

| 3,759,934 A | 9/1973 | Houbihan .................... 260/297 |
| 4,367,236 A | 1/1983 | Grisar et al. ................. 424/273 |
| 4,602,093 A | 7/1986 | Baldwin et al. | |

FOREIGN PATENT DOCUMENTS

| EP | 0 503 785 | 9/1992 |
| WO | WO 95 01967 A | 1/1995 |
| WO | WO 99/54309 | 10/1999 |

OTHER PUBLICATIONS

Gelens et al., 2000, Bioorganic and Medicinal Chemistry Letters, "Solid–phase synthesis of 4–substitutued imidazole using a Scaffold approach", 10: 1935–1938.*
Tasaka et al., 1999, CAS: 131:299449.*
Iwasaki et al., 1976. Helvetica Chemica Acta. 59(8). p. 2738–2752.*
Iwasaki, S. Photochemical reactions. Part 91. Photochemistry of imidazolides. I. the photo–fries–type rearrangement of N–substituted imidazoles. Helv chim Acta. 1976;59(8):2738–52 (abstract only).*
Bell. et al. "2(1–H)–Quinolinones with Cardiac Stimulant Activity. 3.Synthesis and Biological Properties of 6–Inadol–l–yl Derivatives" J. Med Chem. 32: 1552–1558 (1989).
J. March. ed. Advanced Organic Chemistry.John Wiley & Sons, pp. 935–936 Fourth Edition (1992).
Paul. Rolf et al. "Imidazo[1,5–d][1,2,4]triazines as Potential Antiasthma Agents" J. Med. Chem. vol. 28, pp. 1704–1716 (1985).

\* cited by examiner

*Primary Examiner*—Joseph K. McKane
*Assistant Examiner*—Robert Shiao
(74) *Attorney, Agent, or Firm*—Mark Chao; Elaine M. Ramesh

(57) ABSTRACT

A method for producing a compound of the formula:

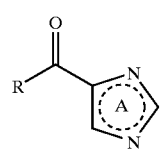

(III)

wherein R is an optionally substituted hydrocarbon group or an optionally substituted heterocyclic group and ring A is an imidazole ring which is optionally substituted further, or a salt thereof, which method comprises reacting a compound of the formula:

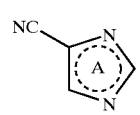

(I)

wherein ring A is as defined above, or a salt thereof, and a compound of the formula:

R—M¹ (II)

wherein $M^1$ is an alkali metal atom or a group of the formula: —Mg—$Y^1$ where $Y^1$ is a halogen atom, and R is as defined above, or a salt thereof, and bringing the resulting product into contact with an acid.

11 Claims, No Drawings

PROCESS FOR THE PREPARATION OF IMIDAZOLE DERIVATIVES

This application is the National Phase filing of International Patent Application No. PCT/JP00/04036, filed Jun. 21, 2000.

TECHNICAL FIELD

The present invention relates to a production method of a naphthalene derivative showing a pharmaceutical effect such as a steroid $C_{17,20}$ lyase inhibitory action and the like, and an intermediate therefor.

BACKGROUND ART

As a synthetic method of a compound wherein an aromatic compound is substituted by an alkanoyl group, for example, the following reactions are known.
(1) JP-A-7-285945 discloses a reaction shown by

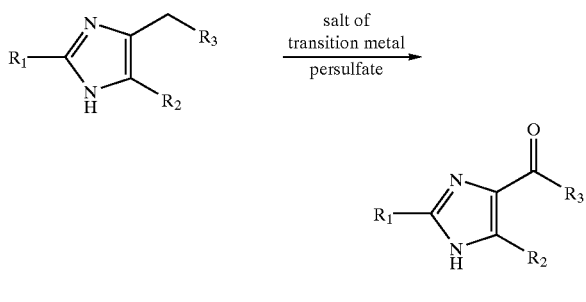

wherein $R_1$ and $R_2$ are each a hydrogen atom, a halogen atom, an alkyl group and the like, and $R_3$ is a hydrogen atom, an alkyl group, an aryl group and the like,
(2) Tetrahedron 49(7), 1431 (1993) discloses a reaction shown by

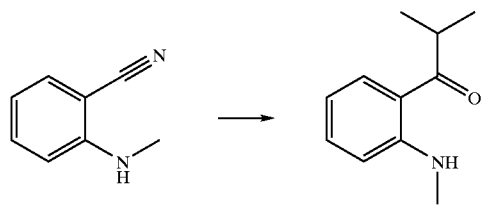

and
(3) J. Org. Chem. 59(17), 4844 (1994) discloses a reaction shown by

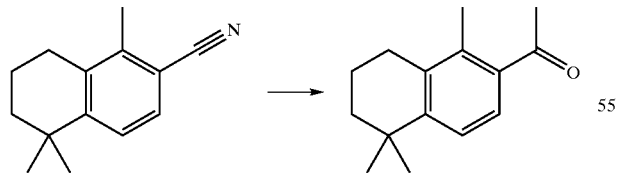

DISCLOSURE OF THE INVENTION

The present inventors have conducted intensive studies of a production method of the compound of the following formula (V) having a superior steroid $C_{17,20}$ lyase inhibitory action and the like and an intermediate therefor, and found that the synthesis of a compound of the following formula (V) from a compound of the following formula (VI) via a compound of the following formula (I) and a compound of the following formula (III) unexpectedly leads to an industrially advantageous production of a compound of the following formula (V), by which the compound can be obtained in a high yield with a less number of steps without using a heavy metal compound.

Accordingly, the present invention relates to:

(1) a method for producing a compound of the formula:

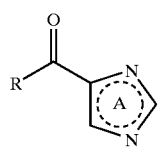

(III)

wherein R is an optionally substituted hydrocarbon group or an optionally substituted heterocyclic group and ring A is an imidazole ring which may-be further substituted, or a salt thereof, which method comprises reacting a compound of the formula:

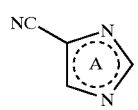

(I)

wherein ring,A is as defined above, or a salt thereof, and a compound of the formula:

(II)

wherein $M^1$ is an alkali metal atom or a group of the formula: —Mg—$Y^1$ ($Y^1$ is a halogen atom) and R is as defined above, or a salt thereof, and bringing the resulting product into contact with an acid;

(2) a method for producing a compound of the formula:

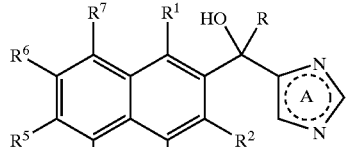

(V)

wherein $R^1$, $R^2$, $R^3$, $R^4$, R5, $R^6$ and $R^7$ are each independently a hydrogen atom, an optionally substituted hydrocarbon group, an optionally substituted hydroxyl group, an optionally substituted thiol group, an optionally substituted amino group, an acyl group or a halogen atom and other symbols are as defined above, or a salt thereof, which method comprises reacting a compound of the formula (III) or a salt thereof and a compound of the formula:

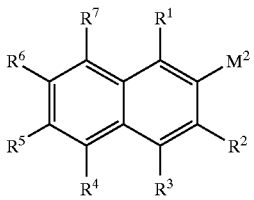

wherein $M^2$ is an alkali metal atom or a group of the formula: —Mg—$y^2$ ($Y^2$ is a halogen atom) and other symbols are as defined above, or a salt thereof;

(3) a method for producing a compound of the formula (V) or a salt thereof, which method comprises reacting compound of the formula (I) or a salt thereof and a compound of the formula (II) or a salt thereof, bringing the resulting product into contact with an acid to give a compound of the formula (III) or a salt thereof, and then reacting this compound and a compound of the formula (IV) or a salt thereof;

(4) a method for producing a compound of the formula (V) or a salt thereof, which method comprises reacting a compound of the formula:

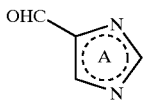

wherein ring A is as defined above, or a salt thereof, and hydroxylamine or a salt thereof, subjecting the resulting product to dehydration to give a compound of the formula (I) or a salt thereof, reacting this compound and a compound of the formula (II) or a salt thereof, bringing the resulting product into contact with an acid to give a compound of the formula (III) or a salt thereof, and reacting this compound and a compound of the formula (Iv) or a salt thereof;

(5) the production method described in the above-mentioned (1), (2), (3) or (4), wherein the ring A of the compounds of the formulas (I), (III), (V) and (VI) is an imidazole ring wherein the 1- or 3-position is optionally protected;

(6) the production method described in the above-mentioned (1), (2), (3) or (4), wherein R is an optionally substituted lower alkyl group, an optionally substituted lower alkenyl group, an optionally substituted cycloalkyl group, an optionally substituted phenyl group or an optionally substituted pyridyl group;

(7) the production method described in the above-mentioned (1), (2), (3) or (4), wherein R is a lower alkenyl group, a cycloalkyl group, a phenyl group, a pyridyl group, or a lower alkyl group optionally substituted by a ha log atom;

(8) the production method described in the above-mentioned (1), (2), (3) or (4), wherein R is a $C_{1-6}$ alkyl group;

(9) the production method described in the above-mentioned (1), (2), (3) or (4), wherein R is an isopropyl group;

(10) the production method described in the above-mentioned (2), (3) or (4), wherein M is sodium, potassium or a group of the formula: —Mg—$Y^2$ ($y^2$ is a halogen atom);

(11) the production method described in the above-mentioned (1), (3) or (4), wherein the reaction product of a compound of the formula (I) or a salt thereof and a compound of the formula (II) or a salt thereof is brought into contact with a sulfuric acid;

(12) the production method described in the above-mentioned (1), (3) or (4), wherein not less than 3 equivalents of the compound of the formula (II) or a salt thereof is used per one equivalent of the compound of the formula (I) or a salt thereof;

(13) the production method described in the above-mentioned (1), (3) or (4), wherein the compound of the formula (I) or a salt thereof and the compound of the formula (II) or a salt thereof are reacted in tetrahydrofuran;

(14) the production method described in the above-mentioned (1), (3) or (4) wherein the compound of the formula (I) or a salt thereof and the compound of the formula (II) or a salt thereof are reacted in not less than 50 equivalents of a solvent relative to one equivalent of the compound of the formula (I) or a salt thereof;

(15) a compound of the formula:

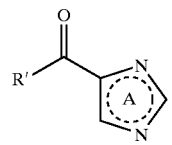

wherein R' is an optionally substituted alkyl group having 3 or more carbon atoms, or a salt thereof;

(16) the compound of the above-mentioned (15), wherein R' is an optionally substituted branched alkyl group having 3 or more carbon atoms;

(17) 1-(1H-imidazol-4-yl)-2-methyl-1-propanone or a salt thereof; and the like.

In the above-mentioned formulas, the alkali metal atom shown by $M^1$ and $M^2$ includes, for example, sodium atom, potassium atom, lithium atom and the like.

The halogen atom shown by $Y^1$ and $y^2$ includes, for example, fluorine atom, chlorine atom, bromine atom, iodine atom and the like.

In the above-mentioned formulas (I), (III), (IIIa), (V) and (VI), the ring A is an imidazole ring which may be further substituted, and the formula:

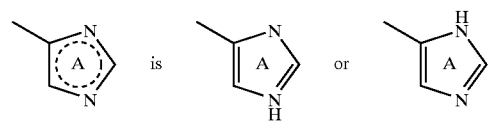

and may have additional substituent(s) besides the substituent(s) already present on the ring.

As the optional and additional substituent(s), 1 to 3 substituent(s) may be present at substitutable position(s) of the nitrogen atom and/or the carbon atom forming the imidazole ring. The group that substitutes the nitrogen atom includes those known as amino-protecting groups that do not affect this reaction, such as $C_{7-20}$ aralkyl (e.g., benzyl, trityl, phenylethyl, benzhydryl etc.) and the like. These protecting groups may have additional substituent(s) at substitutable optional position(s). Such substituent includes halogen atom (e.g., fluorine, chlorine, bromine, iodine e t ), nitro group, methoxy group and the like, wherein the number of the substituent(s) is generally 1 to 3. These protecting groups can be removed easily by hydrolysis, oxidation, reduction and a typical removing method. The group that substitutes carbon atom of the ring A includes, for example, an optionally substituted lower alkyl group, an optionally substituted lower alkoxy group, an optionally substituted alkylsulfonyl group, an optionally substituted carbamoyl group, an optionally substituted sulfamoyl group and the like. The optionally substituted lower alkyl includes, for example, unsubstituted $C_{1-4}$ alkyl group such as methyl, ethyl, propyl and the like, and alkyl group having substituent(s) such as halogeno-$C_{1-4}$ alkyl group and the like, which is exemplified by bromomethyl, difluoroethyl and the like. The optionally substituted lower alkoxy group includes unsubstituted $C_{1-4}$ alkoxy group such as methoxy, ethoxy, propoxy, isopropoxy and the like, and alkoxy group having substituent(s) such as halogeno-$C_{1-4}$ alkoxy group and the like, which is exemplified by chloromethoxy, bromoethoxy and the like. The optionally substituted alkylsulfonyl group includes, for example, unsubstituted $C_{1-4}$ alkylsulfonyl group such as methylsulfonyl, ethylsulfonyl and the like, and alkylsulfonyl group having substituent(s) such as $C_{1-4}$ alkoxy-$C_{1-4}$ alkylsulfonyl group and the like, which is exemplified by methoxymethylsulfonyl and the like. The optionally substituted carbamoyl group includes, for example, besides the unsubstituted carbamoyl group, carbamoyl group having substituent(s) such as mono- or di-$C_{1-4}$ alkylcarbamoyl group (e.g., methylcarbamoyl, ethylcarbamoyl, dimethylcarbamoyl, diethylcarbamoyl etc.), mono- or di-$C_{6-14}$ arylcarbamoyl group (e.g., phenylcarbamoyl, diphenylcarbamoyl etc.), mono- or di-$C_{7-16}$ aralkylcarbamoyl group (e.g., benzylcarbamoyl, dibenzylcarbamoyl etc.) and the like. The optionally substituted sulfamoyl group includes, for example, besides the unsubstituted sulfamoyl group, sulfamoyl group having substituent(s) such as mono- or di-$C_{1-4}$ alkylsulfamoyl group (e.g., methylsulfamoyl, ethylsulfamoyl, dimethylsulfamoyl, diethylsulfamoyl etc.), mono- or di-$C_{6-14}$ arylsulfamoyl group (e.g., phenylsulfamoyl, diphenylsulfamoyl etc.), mono- or di-$C_{7-16}$ aralkylsulfamoyl group (e.g., benzylsulfamoyl, dibenzylsulfamoyl etc.) and the like.

The "hydrocarbon group" of the "optionally substituted hydrocarbon group" shown by R includes, for example, hydrocarbon chain group, cyclic hydrocarbon group and the like.

The hydrocarbon chain group shows, for example, linear or branched hydrocarbon chain group having 1 to 10 carbon atoms, and the like, which is exemplified by alkyl group, alkenyl group, alkynyl group and the like. Of these, alkyl group is particularly preferable. Examples of the "alkyl group" include $C_{1-10}$ alkyl group such as methyl, ethyl, n-propyl, isopropyl, butyl, isobutyl, sec-butyl, tert-butyl, n-pentyl, isopentyl, neopentyl, n-hexyl, isohexyl and the like, and the like, with preference given to $C_{1-6}$ alkyl group (e.g., methyl, ethyl, n-propyl, isopropyl, n-butyl, sec-butyl, tert-butyl etc.). Examples of the "alkenyl group" include $C_{2-10}$ alkenyl group such as vinyl, 1-propenyl, allyl, isopropenyl, 1-butenyl, 2-butenyl, 3-butenyl, isobutenyl, sec-butenyl and the like, and the like, with preference given to $C_{2-6}$ alkenyl group (e.g., vinyl, 1-propenyl, allyl etc.). Examples of the "alkynyl group" include $C_{2-10}$ alkynyl group such as ethynyl, 1-propynyl, propargyl and the like, and the like, with preference given to $C_{2-6}$ alkynyl group (e.g., ethynyl etc.).

The cyclic hydrocarbon group includes, for example, cyclic hydrocarbon group having 3 to 18 carbon atoms, such as alicyclic hydrocarbon group, aromatic hydrocarbon group and the like.

The "alicyclic hydrocarbon group" includes, for example, monocyclic or fused polycyclic group consisting of 3 to 10 carbon atoms, such as cycloalkyl group, cycloakenyl group and di- or tricyclic fused ring group wherein the cycloalkyl group, cycloalkenyl group and $C_{6-14}$ aromatic hydrocarbon (e.g., benzene etc.) and the like are fused, and the like. The "cycloalkyl group" includes, for example, $C_{3-6}$ cycloalkyl group such as cyclopropyl, cyclobutyl, cyclopentyl, cyclohexyl and the like, and the like, the "cycloalkenyl group" includes, for example, $C_{3-6}$ cycloalkenyl group such as cyclopropenyl, cyclobutenyl, cyclopentenyl, cyclohexenyl and the like, and the like, and the fused ring group includes, for example, indanyl and the like.

The "aromatic hydrocarbon group" may be, for example, monocyclic aromatic hydrocarbon group or fused polycyclic aromatic hydrocarbon group consisting of 6 to 18 carbon atoms, and the like. Specific examples include $C_{6-14}$ aryl group such as phenyl, 1-naphthyl, 2-naphthyl, 2-indenyl, 2-anthryl and the like, with preference given to $C_{6-10}$ aryl group (e.g., phenyl etc.) and the like.

The substituent that the "hydrocarbon group" of the "optionally substituted hydrocarbon group" may have is(are) not particularly limited as long as the object of the present invention is achieved. For example, halogen atom, hydroxy group, alkoxy group, acyloxy group, alkylthio group, alkylsulfonyl group, mono- or di-alkylamino group, acylamino group, carboxyl group, alkoxycarbonyl group, oxo group, cycloalkyl group, aryl group, aromatic heterocyclic group and the like are mentioned. These substituents are present at chemically acceptable positions on the "hydrocarbon group" and the number of the substituent(s) is 1 to 5, preferably 1 to 3. When the number of the substituents is 2 or more, they may be the same or different.

When the "hydrocarbon group" of the "optionally substituted hydrocarbon group" is a "hydrocarbon chain group", the substituent(s) that the "hydrocarbon chain group" may have is(are) not particularly limited as long as the object of the present invention is achieved. For example, halogen atom, hydroxy group, alkoxy group, acyloxy group, alkylthio group, acylamino group, carboxyl group, alkoxycarbonyl group, cycloalkyl group, aryl group, aromatic heterocyclic group and the like are mentioned. These substituents are present at chemically acceptable positions on the "hydrocarbon chain group" and the number of the substituent(s) is 1 to 5, preferably 1 to 3. When the number of the substituents is 2 or more, they may be the same or different.

When the "hydrocarbon group" of the "optionally substituted hydrocarbon group" is a "cyclic hydrocarbon group", the substituent(s) that the "cyclic hydrocarbon group" may have is(are) not particularly limited as long as the object of the present invention is achieved. For example, halogen atom, oxo group, hydroxy group, alkoxy group, acyloxy group, alkylthio group, alkylsulfonyl group, mono- or di-alkylamino group, acylamino group, carboxyl group, alkoxycarbonyl group, alkyl group, cycloalkyl group, aryl group, aromatic heterocyclic group and the like are mentioned. These substituents are present at chemically acceptable positions on the "cyclic hydrocarbon group" and the number of the substituent(s) is 1 to 5, preferably 1 to 3. When the number of the substituents is 2 or more, they may be the same or different.

The "halogen atom" used as the "substituent" of the "optionally substituted hydrocarbon group" includes, for example, fluorine, chlorine, bromine, iodine and the like, the "alkoxy group" includes, for example, $C_{1-10}$ alkoxy group such as methoxy, ethoxy, propoxy, isopropoxy, butoxy, isobutoxy, sec-butoxy, pentyloxy, hexyloxy and the like, and the like, the "acyloxy group" includes, for example, $C_{1-10}$ alkyl-carbonyloxy (e.g., acetoxy, propionyloxy etc.) and the like, the "alkylthio groups" includes, for example, $C_{1-10}$ alkylthio group such as methylthio, ethylthio, propylthio, isopropylthio and the like, and the like, the "alkylsulfonyl group" includes, for example, $C_{1-10}$ alkylsulfony group such as methylsulfonyl, ethylsulfonyl, propylsulfonyl and the like, and the like, the mono- or di-alkylamino group includes, for example, $C_{1-4}$ alkylamino group such as methylamino, ethylamino, propylamino and the like, di $C_{1-4}$ alkylamino group such as dimethylamino, diethylamino and the like, the "acylamino group" includes, for example, mono- or di-$C_{1-10}$ alkyl-carbonylamino (e.g., acetylamino, propionylamino, butyrylamino, diacetylamino etc.) and the like, the "alkoxycarbonyl group" includes, for example, $C_{1-10}$ alkoxy-carbonyl group such as methoxycarbonyl, ethoxycarbonyl, propoxycarbonyl, isopropoxycarbonyl, butoxycarbonyl and the like, and the like, the "cycloalkyl group" includes, for example, $C_{3-10}$ cycloalkyl group such as cyclopropyl, cyclobutyl, cyclopentyl, cyclohexyl and the like, and the like, the "aryl group" includes, for example, $C_{6-14}$ aryl group such as phenyl, 1-naphthyl, 2-naphthyl and the like, and the like, the "aromatic heterocyclic group" includes, for example, mono to tricyclic aromatic heterocyclic group having, besides the carbon atom, 1 or 2 kinds of preferably 1 to 4 heteroatom(s) selected from nitrogen, oxygen and sulfur, and the like. Specific examples include thienyl, pyridyl, furylpyrazinyl, pyrimidinyl, imidazolyl, pyrazolyl, thiazolyl, isothiazolyl, oxazolyl, isooxazolyl, pyridazinyl, tetrazolyl, quinolyl, indolyl, isoindolyl and the like. The "alkyl group" includes, for example, $C_{1-10}$ alkyl group such as methyl, ethyl, propyl, isopropyl, butyl, sec-butyl, tert-butyl, pentyl and the like, and the like.

Of the substituents that the aforementioned "hydrocarbon group" may have, alkoxy group, acyloxy group, alkylthio group, alkylsulfonyl group, mono- or di-alkylamino group, acylamino group, carboxyl group, alkoxycarbonyl group, alkyl group, cycloalkyl group, aryl group and aromatic heterocyclic group may further have 1 to 5, preferably 1 to 3, additional substituent(s) at chemically acceptable position (s). Such substituents include, for example, halogen atom (e.g., fluorine, chlorine, bromine etc.), hydroxy group and $C_{1-6}$ alkoxy group (e.g., methoxy, ethoxy, propoxy, isopropoxy etc.).

The heterocyclic group of the "optionally substituted heterocyclic group" shown by R may be, for example, a saturated or unsaturated 4 to 8-membered monocyclic heterocyclic group having, as an atom constituting the ring besides the carbon atom, at least one, preferably 1 to 4, heteroatom(s) such as nitrogen atom, sulfur atom, oxygen atom and the like, or a fused heterocyclic group thereof. Examples thereof include thienyl(2-thienyl, 3-thienyl), pyridyl(2-pyridyl, 3-pyridyl, 4-pyridyl), furyl(2-furyl, 3-furyl), pyrazinyl, 2-pyrimidinyl, 3-pyrrolyl, imidazolyl(1-imidazolyl, 2-imidazolyl, 4-imidazolyl, 5-imidazolyl), 1-pyrazolyl, thiazolyl(2-thiazolyl, 4-thiazolyl, 5-thiazolyl), isothiazolyl(3-isothiazolyl, 4-isothiazolyl), oxazolyl(2-oxazolyl, 4-oxazolyl, 5-oxazolyl), isooxazolyl(3-isooxazolyl), 3-pyridazinyl, benzothienyl and the like. Of these, a monocyclic aromatic heterocyclic group, such as 2-pyridyl, 3-pyridyl, 4-pyridyl, 1-imidazolyl, 4-imidazolyl and the like, is preferable.

The substituent of the "optionally substituted heterocyclic group" shown by R may have 1 to 3 substituent(s) at substitutable position(s) of the heterocyclic group. The substituent may be, for example, alkyl group optionally substituted by 1 to 5 halogen atom(s) (e.g., fluorine, chlorine, bromine, iodine) [e.g., $C_{1-4}$ alkyl such as methyl, ethyl, propyl and the like, halogeno $C_{1-4}$ alkyl such as 2,2,2-trifluoroethyl, 2,2,3,3,3-pentafluoropropyl and the like), $C_{1-4}$ alkoxy group such as methoxy, ethoxy, propoxy, isopropoxy and the like, halogen atom such as chlorine atom, fluorine atom and the like, hydroxy group, amino group, nitro group and the like.

Examples of preferable R include, of the aforementioned examples, an optionally substituted lower alkyl group (having 1 to 4 carbon atoms), an optionally substituted lower alkenyl group (having 1 to 4 carbon atoms), an optionally substituted cycloalkyl group (having 3 to 6 carbon atoms), an optionally substituted phenyl group and an optionally substituted pyridyl group, with particular preference given to lower alkenyl group (having 1 to 4 carbon atoms), cycloalkyl group (having 3 to 6 carbon atoms), phenyl group, pyridyl group and lower alkyl group (having 1 to 4 carbon atoms) optionally substituted by halogen.

The "optionally substituted alkyl group having not less than 3 carbon atoms" shown by R' may be, for example, n-propyl, isopropyl, n-butyl, isobutyl, t-butyl, n-pentyl, isopentyl, n-hexyl, n-heptyl, n-octyl and the like, with preference given to those having 3 to 6 carbon atoms.

The substituent, which the "alkyl group having not less than 3 carbon atoms" of the "optionally substituted alkyl group having not less than 3 carbon atoms" shown by R' has, is exemplified by those mentioned with regard to the aforementioned substituents of the "hydrocarbon group" of the "optionally substituted hydrocarbon group" shown by R. As R', unsubstituted alkyl group having not less than 3 carbon atoms is preferable.

The optionally substituted hydroxyl group shown by $R^1$, $R^2$, $R^3$, $R^4$, $R^5$, $R^6$ and $R^7$ is, for example, besides the unsubstituted hydroxyl group, a substituted hydroxyl group, including, for example, an optionally substituted lower alkoxy such as (1) unsubstituted $C_{1-4}$ alkoxy group (e.g., methoxy, ethoxy, propoxy etc.), (2) lower alkoxy(lower) alkoxy group ($C_{1-4}$ alkoxy-$C_{1-4}$ alkoxy group) (e.g., methoxymethoxy, ethoxymethoxy, methoxyethoxy, ethoxyethoxy etc.), (3) lower alkanoyloxy(lower)alkoxy group ($C_{1-4}$ alkanoyloxy-$C_{1-4}$ alkoxy group) (e.g., acetyloxymethoxy, propionyloxymethoxy, acetyloxyethoxy, propionyloxyethoxy etc.), and the like, and (4) lower ($C_{1-4}$) alkoxy group optionally substituted by 1 to 4 fluorine atom(s) (e.g., fluoromethoxy, difluoromethoxy, trifluoromethoxy, 1-fluoromethoxy, 2-fluoromethoxy, 2,2-difluoroethoxy and the like), lower alkanoyloxy (e.g., $C_{1-4}$ alkanoyloxy such as acetyloxy, propionyloxy etc.), $C_{7-10}$ aralkyloxy (e.g., benzyloxy, phenethyloxy etc.), an optionally substituted carbamoyloxy (e.g., unsubstituted carbamoyloxy and carbamoyloxy substituted by one or two $C_{1-4}$ alkyl group(s), such as methylcarbamoyloxy, ethylcarbamoyloxy, dimethylcarbamoyloxy, diethylcarbamoyloxy, methylethylcarbamoyloxy and the like), and the like.

The optionally substituted thiol group shown by $R^1$, $R^2$, $R^3$, $R^4$, $R^5$, $R^6$ and $R^7$ may be, for example, besides the unsubstituted thiol group, substituted thiol group such as lower alkylthio (e.g., $C_{1-4}$ alkylthio group such as methylthio, ethylthio, propylthio and the like), lower alkanoylthio (e.g., $C_{1-4}$ alkanoylthio such as acetylthio, propionylthio and the like), and the like.

The optionally substituted amino group shown by $R_1$, $R^2$, $R^3$, $R^4$, $R^5$, $R^6$ and $R_7$ may be, for example, besides the unsubstituted amino group, substituted amino group such as lower alkylamino (e.g., $c_{1-4}$ alkylamino group such as methylamino, ethylamino, propylamino and the like), di(lower)alkylamino (e.g., di($C_{1-4}$)alkylamino such as dimethylamino, diethylamino and the like), $C_{1-4}$ alkanoylamino (e.g., acetamide, propionamide etc.) and the like.

The acyl group shown by $R^1$, $R^2$, $R^3$, $R^4$, $R^5$, $R^6$ and $R_7$ may be, for example, alkylsulfonyl group (e.g., $C_{1-4}$ alkylsulfonyl such as methylsulfonyl, ethylsulfonyl and the like), an optionally substituted carbamoyl group such as mono- or di($C_{1-10}$)alkylcarbamoyl group (e.g., methylcarbamoyl, ethylcarbamoyl, propylcarbamoyl, isopropylcarbamoyl, cyclopropylcarbamoyl, dimethylcarbamoyl, diethylcarbamoyl etc.), mono- or di($C_{6-14}$)arylcarbamoyl (e.g., phenylcarbamoyl, diphenylcarbamoyl etc.), mono- or di($C_{7-16}$)aralkylcarbamoyl group (e.g., benzylcarbamoyl, dibenzylcarbamoyl etc.), an optionally substituted sultamoyl such as mono- or di($C_{1-10}$)alkylsulfamoyl group (e.g., methylsulfamoyl, ethylsulfamoyl, dimethylsulfamoyl, diethylsulfamoyl etc.), mono- or di($C_{6-14}$)arylsulfamoyl group (e.g., phenylsulfamoyl, diphenylsulfamoyl etc.), mono- or di($C_{7-16}$)aralkylsulfamoyl group (e.g., benzylsulfamoyl, dibenzylsulfamoyl etc.), and the like.

The halogen shown by $R^1$, $R^2$, $R^3$, $R^4$, $R^5$, $R^6$ and $R^7$ is exemplified by fluorine, chlorine, bromine, iodine and the like.

The "optionally substituted hydrocarbon group" shown by $R^1$, $R^2$, $R^3$, $R^4$, $R^5$, $R^6$ and $R^7$ is exemplified by those similar to the "optionally substituted hydrocarbon group" shown by R. Of those, an optionally substituted lower alkyl group is preferable, which is exemplified by optionally substituted chain or cyclic $C_{1-6}$ alkyl group (e.g., methyl, ethyl, propyl, isopropyl, cyclopropyl, butyl, isobutyl, sec-butyl, tert-butyl, pentyl, cyclopentyl, hexyl etc.). The $C_{1-6}$ alkyl group may have 1 to 5 substituent(s) at substitutable position(s). Examples of the substituent include, halogen (e.g., fluorine, chlorine, bromine etc.), $C_{1-4}$ alkoxy group (e.g., methoxy, ethoxy, propoxy etc.), hydroxyl group and the like.

Examples of preferable $R^1$, $R^2$, $R_3$, $R^4$, $R^5$, $R_6$ and $R_7$ include hydrogen atom, optionally substituted hydrocarbon group, optionally substituted hydroxyl group, optionally substituted amino group and halogen atom from among those mentioned above, more preferably hydrogen atom, optionally substituted hydrocarbon group, optionally substituted hydroxyl group and halogen atom.

Of those mentioned above, $R^5$ is preferably (1) an optionally substituted hydroxyl group such as (i) lower alkanoyloxy group, (ii) lower alkanoyloxy(lower)alkoxy group, (iii) lower alkoxy group, (iv) lower alkoxy(lower)alkoxy group, (v) lower alkoxy group optionally substituted by 1 to 4 fluorine atom(s) and (vi) benzyloxy group etc.), (2) a halogen atom, (3) a lower alkyl group optionally substituted by hydroxyl group, )4) a lower alkynyl group, (5) a lower alkanoyl group, (6) an amino group optionally substituted by lower alkanoyl group, lower alkylaminocarbonyl group and lower alkylsulfonyl group, (7) lower alkylthio group or (8) mono- or di($C_{1-10}$)alkylcarbamoyl, more preferably a lower alkyl group, a lower alkoxy group, a lower alkanoylamino group or a mono- or di($C_{1-10}$)alkylcarbamoyl, and most preferably, a methoxy group. $R^6$ is preferably a hydrogen atom, a lower alkyl group or a lower alkoxy, more preferably, a hydrogen atom or a lower alkoxy. $R^4$ is preferably (1) a hydrogen atom, (2) a halogen atom, (3) a lower alkoxy group or (4) a lower alkyl group optionally substituted by hydroxyl group, more preferably, a hydrogen atom or a lower alkyl group.

As the combination of $R^1$, $R^2$, $R^3$, $R^4$, $R_5$, $R^6$ and $R^7$, it is preferable that 1 to 3 thereof be each independently an optionally substituted lower alkyl group, an optionally substituted hydroxyl group, an optionally substituted amino group or a halogen atom, and it is more preferable that 1 to 3 thereof be each independently an optionally substituted lower alkyl group or an optionally substituted hydroxyl group.

It is preferable that any of $R^4$, $R^5$ and $R^6$ be a lower alkyl group or a lower alkoxy group, and all of $R^1$, $R^2$, $R^3$ and $R^7$ be each a hydrogen atom.

In the compounds of the above-mentioned formulas (I), (II), (III), (IIIa), (IV), (V) and (VI), when the substituent of the substituent shown by R, R', $R^1$, $R^2$, $R^3$, $R^4$, $R^5$, $R^6$ and $R_7$ or the substituent of ring A has an amino group, a hydroxyl group or a carboxyl group, it may be protected by a group known to be a protecting group thereof.

The amino-protecting group is exemplified by those mentioned above with regard to the group that substitutes on the nitrogen atom as an atom constituting the ring in the aforementioned ring A.

The carboxyl-protecting group includes, for example, optionally substituted, $C_{1-6}$ alkyl (e.g., methyl, ethyl, propyl, isopropyl, butyl, tert-butyl etc.), phenyl, trityl, silyl and the like. These substituents may be halogen atom (e.g., fluorine, chlorine etc.), nitro group and the like, and the number of the substituent(s) is generally 1 to 3.

The hydroxy-protecting group includes, for example, optionally substituted, $C_{1-6}$ alkyl (e.g., methyl, ethyl, propyl, isopropyl, butyl, tert-butyl etc.), phenyl, $C_{7-10}$ aralkyl (e.g., phenyl-$C_{1-4}$ alkyl such as benzyl and the like), phenyloxycarbonyl, benzoyl, ($C_{7-10}$ aralkyloxy)carbonyl (e.g., phenyl-$C_{1-4}$ alkyloxy-carbonyl such as benzyloxycarbonyl and the like), pyranyl, furanyl or silyl and the like. These substituents may be a halogen atom (e.g., fluorine, chlorine etc.), $C_{1-6}$ alkyl (e.g., methyl, ethyl, propyl etc.), phenyl, $C_{7-10}$ aralkyl (e.g., phenyl-$C_{1-4}$ alkyl such as benzyl and the like), nitro group and the like and the number of the substituent(s) is generally 1 to 4.

Unless otherwise specified, the "lower" in lower alkyl group, lower alkoxy group and the like in the present specification means chain, branched or ring having 1 to 6 carbon atoms.

A compound of the formula (III) or a salt thereof [hereinafter sometimes to be simply referred to as compound (III)] can be produced by reacting a compound of the formula (I) or a salt thereof [hereinafter sometimes to be simply referred to as compound (I)] and a compound of the formula (II) or a salt thereof [hereinafter sometimes to be simply referred to as compound (II)], and bringing the resulting product into contact with an acid.

Since the compounds of the formulas (I) and (III) contain a nitrogen atom as an atom constituting the ring A, they can form a salt. Such salt is, for example, inorganic acid salts such as hydrochloride, sulfate, hydrobromate, phosphate and the like, organic acid salts such as acetate, trifluoroacetate, succinate, maleate, fumarate, propionate, citrate, tartrate, lactate, oxalate, methanesulfonate, p-toluenesulfonate and the like. When the substituent of the ring A in the formula (I), R in the formula (II), or R or ring A in the formula (III) has an acidic group such as carboxyl group and the like, these compounds can form, for example, alkali metal salt such as potassium salt, sodium salt, lithium salt and the like, alkaline earth metal salt such as calcium salt, magnesium salt and the like, salt with organic base such as ammonium salt, trimethylamine salt, triethylamine salt, tert-butyldimethylamine salt, dibenzylmethylamine salt, benzyldimethylamine salt, N,N-dimethylaniline salt, pyridine salt, quinoline salt and the like.

The reaction between compound (I) and compound (II) is generally carried out in a solvent. Examples of the solvent include an organic solvent inert to the reaction, such as ethers (e.g., diethyl ether, dioxane, tetrahydrofuran etc.), saturated hydrocarbons (e.g., hexane, pentane etc.), aromatic hydrocarbons (e.g., benzene, toluene etc.), halogenated hydrocarbons (e.g., dichloromethane, chloroform etc.) and the like. Of these, ethers such as tetrahydrofuran and the like are preferable. The amount of the solvent to be used is generally about 1–150 equivalents, particularly 50 to 60 equivalents, per 1 equivalent of compound (I). The amount of the compound (II) to be used is generally about 1 to 20 equivalents, preferably not less than 3 equivalents, particularly preferably 3 to 3.2 equivalents, per 1 equivalent of compound (I). The reaction temperature is from −20° C. to 100° C., preferably 10 to 50° C., and the reaction time is about 5 minutes to 48 hours, preferably 1 to 5 hours. The product resulting from this reaction may be used as a starting material of the next reaction, after isolation by a conventional method or as a reaction mixture.

The obtained product is brought into contact with an acid to produce compound (III).

The acid is, for example, inorganic acid such as hydrochloric acid, sulfuric acid and the like. Of these, sulfuric acid is preferable. In this case, addition of water to the reaction system generally promotes the reaction and is preferable. The amount of acid to be added is generally 1 to 50 equivalents, preferably not less than 3 equivalents (3 to 10 equivalents), per 1 equivalent of compound (I), and the amount of water to be added is not less than 1 equivalent, preferably not less than 3 equivalents, per 1 equivalent of compound (I). These acids are brought into contact with the resulting product generally by adding an aqueous solution (aqueous solution having an acid concentration of generally 1 to 80 wt %, preferably 5 to 20 wt %) to the reaction mixture containing the product. The use of aqueous sulfuric acid solution (aqueous solution having an acid concentration of generally 1 to 80 wt %, preferably 5 to 20 wt %, 3 to 4 equivalents by conversion to sulfuric acid) per 1 equivalent of compound (I) is preferable.

When compound (III) thus obtained is in a free state, it may be converted to a salt by a conventional method. When the compound is obtained as a salt, it may be converted to a free compound or a different salt by a conventional method. When the compound has a protecting group, it may be deprotected by a conventional method to be mentioned below. The compound (III) thus obtained can be isolated and purified from a reaction mixture by a known method, such as redissolution, concentration, solvent extraction, fractional distillation, crystallization, recrystallization, chromatography and the like. Alternatively, it can be subjected to the next step as a reaction mixture without isolation. The compound of the formula (IIIa) or a salt thereof [hereinafter sometimes to be simply referred to as compound (IIIa)] contained in the objective compound (III) of this reaction is a novel compound. Of the compounds (IIIa), a compound wherein R' is an optionally substituted branched alkyl having not less tan 3 carbon atoms (e.g., $C_{3-6}$ alkyl such as isopropyl, isobutyl, t-butyl, sec-butyl etc.) is preferable, and particularly 1-(1H-imidazol-4-yl)-2-methyl-1-propanone and a salt thereof are preferable. The compound (III) is useful as a synthetic intermediate for various compounds.

A compound of the formula (V) or a salt thereof (hereinafter sometimes to be simply referred to as compound (V)] can be produced by reacting compound (III) and a compound of the formula (IV) or a salt thereof [hereinafter sometimes to be simply referred to as compound (IV)]. Since the compound of the formula (V) contains a nitrogen atom as an atom constituting the ring A, it can form a salt. Examples of such salt include inorganic acid salts such as hydrochloride, sulfate, hydrobromate, phosphate and the like, and organic acid salts such as acetate, trifluoroacetate, succinate, maleate, fumarate, propionate, citrate, tartrate, lactate, oxalate, methanesulfonate, p-toluenesulfonate and the like. When the substituents of $R^1$, $R^2$, $R^3$, $R^4$, $R^5$, $R^6$ and $R^7$ in the formula (IV), the substituents of R, $R^1$, $R^2$, $R^3$, $R^4$, $R^5$, $R^6$ and $R^7$ in the formula (V) or the substituent of ring A has an acidic group, such as carboxyl group and the like, these compounds can form, for example, alkali metal salts such as potassium salt, sodium salt, lithium salt and the like, alkaline earth metal salts such as calcium salt, magnesium salt and the like, salts with organic base such as ammonium salt, trimethylamine salt, triethylamine salt, tert-butyldimethylamine salt, dibenzylmethylamine salt, benzyldimethylamine salt, N,N-dimethylaniline salt, pyridine salt, quinoline salt and the like.

The reaction between compound (III) and compound (IV) is preferably carried out generally in a solvent. Examples of the solvent include an organic solvent inert to the reaction, such as ethers (e.g., diethyl ether, dioxane, tetrahydrofuran etc.), saturated hydrocarbons (e.g., hexane, pentane etc.), aromatic hydrocarbons (e.g., benzene, toluene etc., halogenated hydrocarbons (e.g., dichloromethane, chloroform etc.) and the like. Of these, ethers such as tetrahydrofuran and the like are preferable. The amount of the solvent to be used is particularly preferably 50 to 60 equivalents, per 1 equivalent of compound (III). The amount of the compound (IV) to be used is about 1 to 20 equivalents, generally not less than 2.5 equivalents, preferably 2.8 to 3.0 equivalents, per 1 equivalent of compound (III). The reaction temperature is from −20° C. to 100° C., preferably 10 to 50° C., and the reaction time is generally 5 minutes to 48 hours, preferably 1 to 5 hours.

The compound (V) can be obtained easily from the resulting reaction mixture by converting $M^2$ to H by a conventional method. As a conventional method to convert $M^2$ to H, for example, hydrolysis, solvolysis and the like are used. The solvent to be used for hydrolysis and solvolysis is, for example, a protic solvent (e.g., water, lower alcohol such as methanol, ethanol, propanol, isopropanol, butanol and the like that dissociates and releases proton easily, or a mixture thereof). An acid may be present at this time. The acid includes, for example, inorganic acid such as hydrochloric acid, sulfuric acid and the like, and the like. Generally, compound (V) can be produced by adding a protolytic solvent to the reaction mixture. When a protolytic solvent is added to the reaction mixture, it is preferably added by small portions. The amount of the protolytic solvent to be added is not less than one equivalent (1 to 50 equivalents), preferably not less than 3 equivalents (3 to 10 equivalents), per 1 equivalent of compound (III). In this case, the reaction temperature is generally −20° C. to 100° C., preferably 10° C. to 50° C., and the reaction time is 5 minutes to 24 hours, preferably about 10 minutes to 1 hour.

When compound (V) thus obtained is in a free state, it may be converted to a salt by a conventional method. When the compound is obtained as a salt, it may be converted to a free compound or a different salt by a conventional method. When the compound has a protecting group, it may be deprotected by a conventional method to be mentioned below. The compound (V) thus obtained can be isolated and purified from a reaction mixture by a known method, such as redissolution, concentration, solvent extraction, fractional distillation, crystallization, recrystallization, chromatography and the like.

The compound of the present specification, such as compound (V) and the like, may have one or more asymmetric carbons in a molecule. An R configuration and an S configuration are present with regard to each of these asymmetric carbons, which can be resolved as necessary by a conventional method.

A starting material compound (I) can be produced by reacting a compound of the formula (VI) or a salt thereof

[hereinafter sometimes to be simply referred to as compound (VI)] and hydroxylamine or a salt thereof.

The salt of the compound of the formula (VI) and hydroxylamine may be, for example, inorganic acid salts such as hydrochloride, sulfate, hydrobromate, phosphate and the like, organic acid salts such as acetate, trifluoroacetate, succinate, maleate, fumarate, propionate, citrate, tartrate, lactate, oxalate, methanesulfonate, p-toluenesulfonate and the like.

When the substituent of the ring A in the formula (VI) has an acidic group, such as carboxyl group and the like, the compound can form, for example, alkali metal salt such as potassium salt, sodium salt, lithium salt and the like, alkaline earth metal salt such as calcium salt, magnesium salt and the like, salt with organic base such as ammonium salt, trimethylamine salt, triethylamine salt, tert-butyldimethylamine salt, dibenzylmethylamine salt, benzyldimethylamine salt, N,N-dimethylaniline salt, pyridine salt, quinoline salt and the like.

The reaction between compound (VI) and hydroxylamine or a salt thereof is generally carried out in a solvent. Examples of the solvent include pyridine solvent, such as pyridine, picoline, lutidine and the like, preferably pyridine and the like. The amount of the solvent to be used is generally 0.1 to 50 equivalents, particularly 0.1 to 1 equivalent, per 1 equivalent of compound (VI). The amount of hydroxylamine or a salt thereof to be used is generally not less than 1 equivalent (1 to 10 equivalents), preferably 1.1 to 1.5 equivalents, per 1 equivalent of compound (VI). The reaction temperature is from 0° C. to 100° C., preferably 20° C. to 50° C., and the reaction time is generally 5 minutes to 48 hours, preferably 1 to 5 hours.

The resulting product is then isolated by a conventional method or the reaction mixture as it is subjected to dehydration, whereby the compound (I) can be produced.

The dehydration can be carried out by, for example, reacting a dehydrating agent with compound (I). Examples of the dehydrating agent include acetic anhydride, phosphorus oxide, phosphorus chloride, thionyl chloride, N,N-dicyclohexylcarbodiimide, N,N-carbonyldiimidazole and the like. Of these, acetic anhydride and the like are preferable. The amount of use of the dehydrating agent is generally 0.5 to 20 equivalents, preferably 1.0 to 2.0 equivalents, per 1 equivalent of compound (VI). This reaction is advantageously carried out in a solvent. Examples of the solvent include ethers such as diethyl ether, dioxane, tetrahydrofuran and the like, aromatic hydrocarbons such as benzene, toluene and the like, halogenated hydrocarbons such as dichloromethane, chloroform and the like, and the like. It is possible to use the same solvent as used in the reaction of compound (VI) and hydroxylamine or a salt thereof, such as pyridine solvent (e.g., pyridine, picoline, lutidine etc.). The reaction temperature is generally 0° C. to 150° C., preferably 100° C. to 130° C. and the reaction time is generally 5 minutes to 48 hours, preferably 1 to 5 hours.

When compound (I) thus obtained is in a free state, it may be converted to a salt by a conventional method. When the compound is obtained as a salt, it may be converted to a free compound or a different salt by a conventional method. When the compound has a protecting group, it may be deprotected by a conventional method to be mentioned below. The compound (I) thus obtained can be isolated and purified from a reaction mixture by a known method, such as redissolution, concentration, solvent extraction, fractional distillation, crystallization, recrystallization, chromatography and the like. It is also possible to subject the reaction mixture to the next reaction without isolation.

In each of the above-mentioned steps, a protecting group may be introduced, where necessary, into a starting material or the objective compounds (II), (II), (III), (IIIa), (IV), (V) and (VI) or deprotected before or after each reaction. The introduction and deprotection of protecting groups can be conducted by a known method. A protecting group can be eliminated by a method known per se or a method analogous thereto. For example, a reaction with an acid, base, ultraviolet radiation, hydrazine, phenylhydrazine, sodium N-methyldithiocarbamate, tetrabutylammonium fluoride, palladium acetate and the like or reduction and the like are employed. When, for example, compound (V) is protected with a trityl group, the trityl group can be removed by, for example, a treatment under acidic conditions (e.g., heating), or hydrogenolysis and the like. The acid to be used is, for example, organic acid such as formic acid, acetic acid and the like, inorganic acid such as hydrochloric acid and the like, and the like. The reaction may be carried out in a solvent inert to the reaction, such as alcohols, ethers.(e.g., tetrahydrofuran etc.) and the like. The reaction temperature is generally 0° C. to 100° C. and the reaction time is generally 5 minutes to 48 hours, preferably 2 to 6 hours.

According to the method of the present invention, for example, the following compound (V) can be produced industrially advantageously.

1-(1H-Imidazol-4-yl)-1-(6-methoxynaphthalen-2-yl)-2-methylpropanol, 6-(1-hydroxy-1-(1H-imidazol-4-yl)-2-methylpropyl)-N-methyl-2-naphthamide, N-ethyl-6-(1-hydroxy-1-(1H-imidazol-4-yl)-2-methylpropyl)-2-naphthamide, 6-(1-hydroxy-1-(1H-imidazol-4-yl)-2-methylpropyl)-N-isopropyl-2-naphthamide, N-cyclopropyl-6-(1-hydroxy-1-(1H-imidazol-4-yl)-2-methylpropyl)-2-naphthamide, and their salts and the like.

The compound (V) has a superior effect as a pharmaceutical and shows a superior inhibitory activity particularly against steroid $C_{17-20}$ lyase. The compound (V) shows low toxicity and fewer side effects. Therefore, it is useful as an agent for the treatment and prevention of various diseases in mammals (e.g., humans, bovines, horses, dogs, cats, monkeys, mice, rats etc., particularly humans) such as (1) primary carcinoma of malignant tumor (e.g., prostate cancer, breast cancer, uterine cancer, ovarian cancer etc.), and metastatic cancer and recurrent carcinoma thereof, (2) various symptoms associated with these cancers (e.g., pain, cachexia etc.), (3) prostatic hypertrophy, masculinism, hypertrichiasis, male-pattern baldness, male infantile precocity. endonictriosis, hysteromyoma, adenomyosis of uterus, mastopathy, polycystic ovary syndrome and the like.

The compound (V) shows a superior effect even when used alone, and the effect can be reinforced even more when used together with other pharmaceutical preparation and therapeutic method. Examples of the combination drug include, but not limited to, sex hormone agent, alkylating agent, antimetabolite, carcinostatic antibiotic, plant alkaloid, immunotherapeutic drug and the like.

As the therapy to be combined, there are mentioned, for example, operation, thermotherapy, radiation therapy and the like. Together with chemotherapy including administration of the compound (V), for example, a therapeutic method other than chemotherapy, such as an operation inclusive of orchidectomy, thermotherapy, radiation therapy and the like, can be used in combination.

As a pharmacologically acceptable carrier, various organic or inorganic carrier substances in common use as pharmaceutical materials are used by adding them in a suitable amount as excipients, lubricants, binders, disintegrants and thickeners for solid preparations; solvents, dispersants, dissolution aids, suspending agents, isotonicity agents, buffers, soothing agent and the like for liquid preparations. Where necessary, additives such as antiseptics, antioxidants, coloring agents, sweetening agents and the like can be used according to a conventional method. Examples of preferable excipients include lactose, sucrose, D-mannitol, starch, crystalline cellulose, light silicic anhydride and the like. Examples of preferable lubricants include magnesium stearate, calcium stearate, talc, colloidal silica and the like. Examples of preferable binder include crystalline cellulose, sucrose, D-mannitol, dextrin, hydroxypropylcellulose, hydroxypropyl methylcellulose, polyvinylpyrrolidone and the like. Examples of preferable disintegrators include starch, carboxymethyl cellulose, carboxymethyl cellulose calcium, crosslinked carmellose sodium, carboxymethyl starch sodium and the like. Examples of preferable thickener include natural gums, cellulose derivative, polyacrylic acid and the like. Examples of preferable solvents include water for injection, alcohol, propylene glycol, Macrogol, sesame oil, corn oil and the like. Examples of preferable dispersant include Tween 80, HCO 60, polyethylene glycol, carboxymethyl cellulose, alginate sodium and the like. Examples of preferable dissolution aids include polyethylene glycol, propylene glycol, D-mannitol, benzyl benzoate, ethanol, trisaminomethane, cholesterol, triethanolamine, sodium carbonate, sodium citrate and the like. Examples of preferable suspending agents include surfactant (e.g., stearyltriethanolamine, sodium lauryl sulfate, laurylaminopropionic acid, lecithin, benzalkonium chloride, benzethonium chloride, glycerine monostearate etc.), hydrophilic macro molecule (e.g., polyvinyl alcohol, polyvinyl pyrrolidone, carboxymethyl cellulose sodium, methylcellulose, hydroxymethylcellulose, hydroxyethylcelluloser hydroxypropylcellulose etc.) and the like. Examples of preferable isotonicity agents include sodium chloride, glycerine, D-mannitol and the like. Examples of preferable buffers include buffering solutions of phosphate, acetate, carbonate and citrate, and the like. Examples of preferable soothing agents include benzyl alcohol and the like. Examples of preferable antiseptics include p-hydroxybenzoic esters, chlorobutanol, benzyl alcohol, phenethyl alcohol, dehydroacetic acid, sorbic acid and the like. Examples of preferable antioxidants include sulfite, ascorbic acid and the like.

A pharmaceutical preparation containing compound (V) can be produced according to a conventional method. Specific examples are shown in the following.

(1) Tablet, Powder, Granule, Capsule:

Excipient, disintegrator, binder, lubricant or the like is added to compound (V) and the mixture is compression formed. Where necessary, taste masking, enteric coating or a coating for sustained release is applied.

(2) Injection:

The compound (V) is formulated together with, for example, dispersant, preservative, isotonizing agent and the like to give an aqueous injection, or dissolved, suspended or emulsified in a vegetable oil such as olive oil, sesame oil, cottonseed oil, corn oil and the like, propylene glycol and the like and prepared to give an oily injection.

(3) Suppository:

A suppository can be produced by making the compound (V) into an oily or aqueous solid, semisolid or liquid composition. Examples of the oily base to be used for such a composition include glyceride of higher fatty acid (e.g., cacao butter, Witepsol), medium fatty acid (e.g., migliols), vegetable oil (e.g., sesame oil, soybean oil, cottonseed oil etc.) and the like. Examples of the aqueous gel base that can be used for this composition include natural gums, cellulose derivative, vinyl polymer, acrylate polymer and the like.

While the proportion of compound (V) to be contained in these preparations varies depending on the kind of preparation, it is generally 0.01 to 50%.

While the amount of use of compound (V) in the aforementioned pharmaceutical preparation varies depending on the compound to be selected, animal species to be the administration target, administration frequency and the like, compound (V) shows effectiveness over a wide range of application. When, for example, a pharmaceutical preparation containing compound (V) is orally administered to an adult patient with a solid tumor (e.g., patient with prostate cancer), the daily dose in the effective amount of the compound (V) is generally about 0.001 to about 500 mg/kg body weight, preferably about 0.1 to about 40 mg/kg body weight, more preferably about 0.5 to about 20 mg/kg body weight. In the case of parenteral administration and concurrent use with other anticancer agent, the dose is smaller than these. However, the amount of compound (V) actually administered is determined depending on the kind of compound (V), mode of preparation, age, body weight and sex of patient, level of disease, administration route, period and intervals of the administration, and the like, and can be changed any time depending on the judgement of doctors.

The administration route of the aforementioned pharmaceutical preparation is not particularly limited as long as the object can be achieved, but the preparation can be administered orally or parenterally. The term "parenteral" used herein includes intravenous, intramuscular, subcutaneous, intranasal, intradermal, instillation, intracerebral, intrarectal, intravaginal and intraperitoneal administrations and the like.

The period and intervals of the administration of the aforementioned pharmaceutical preparation are modified according to various conditions and determined according to the judgment of doctors at any time. The administration method includes, for example, divisional administration, consecutive daily administration, intermittent administration, administration in large amounts in a short period, repeat administration and the like. In the case of oral administration, for example, the preparation is desirably administered once a day to several times a day (particularly 2 or 3 times a day) by dividing the dose. It is also possible to administer the preparation as a sustained release preparation or an intravenous infusion to be administered over a long time.

BEST MODE FOR CARRYING OUT THE INVENTION

The present invention is explained in more detail by way of the following Examples. These Examples are mere embodiments and do not limit the present invention in any way. They can be modified as long as they do not deviate from the scope of the present invention. In the Examples, the abbreviations mean the following.

S: singlet, d: doublet, t: triplet, q: quartet, dd: double doublet, dt: double triplet, m: multiplet, br: broad, J: coupling constant, room temperature: 0 to 30° C., DMF:

dimethylformamide, THF: tetrahydrofuran, IPE: isopropyl ether.

EXAMPLE 1

Production of 1-(1H-imidazol-4-yl)-2-Methyl-1-Propanone

A solution of 4-cyanoimidazole (42.7 g, 0.458 mol) in THF (500 ml) was added dropwise over 30 min to a solution (1.4 L, 1.47 mol, 3.2 equivalents) of 1.1 M isopropyl magnesium bromide in THF at 0 to 10° C. under a nitrogen atmosphere. The mixture was stirred at 15 to 25° C. for 3 h. Water (430 ml) and 10% aqueous sulfuric acid solution (860 ml) were successively added dropwise, and the mixture was stirred at 30 min. A 30% aqueous sodium hydroxide solution was added dropwise to adjust the pH to 8. After partitioning, the aqueous layer was extracted with ethyl acetate (300 ml×2). The organic layer was combined, and the mixture was washed successively with saturated aqueous sodium hydrogencarbonate and saturated brine, and concentrated under reduced pressure. The concentration residue was broken up with isopropyl ether (300 ml). The crystals were collected by filtration and washed with isopropyl ether. The crystals were dried in vacuo (40° C.) to give 1-(1H-imidazol-4-yl)-2-methyl-1-propanone (51.9 g, yield 82%). $^1$H-NMR (CDCl$_3$): δ 1.25 (6H, d, J=6.9 Hz), 3.36 (1H, quint, J=6.9 Hz), 7.81 (1H, s), 7.87 (1H, s)

EXAMPLE 2

Production of 1-(1H-imidazol-4-yl)-1-(6-Methoxynaphthalen-2-yl)-2-Methylpropanol THF (14 ml) was added to magnesium (0.55 g, 22.4 mmol) under a nitrogen atmosphere. Iodine (3 mg) was added and the mixture was stirred. While keeping the mixture at not higher than 50° C., a solution of 2-bromo-6-methoxynaphthalene (5.15 g, 21.7 mmol.) in THF (12 ml) was added dropwise, and the mixture was stirred at 15 to 25° C. for 1.5 h. A solution of 1-(1H-imidazol-4-yl)-2-methyl-1-propanone (1 g, 7.24 mmol) in THF (5 ml) was added dropwise at −20° C., and the mixture was stirred at 15 to 25° C. for 8 h. A saturated aqueous sodium hydrogencarbonate (5 ml) and water (5 ml) were successively added dropwise. After stirring, the mixture was passed through celite. After partitioning, the aqueous layer was extracted with ethyl acetate (5 ml). The organic layer was combined, and the mixture was washed with saturated brine and concentrated under reduced pressure. The concentration residue was broken up with ethyl acetate (6 ml) and isopropyl ether (12 ml), and the crystals were collected by filtration and washed with isopropyl ether (12 ml). The crystals were dried in vacuo (40° C.) to give 1-(1H-imidazol-4-yl)-1-(6-methoxynaphthalen-2-yl)-2-methylpropanol (1.8 g, yield 84%).

EXAMPLE 3

Production of 1-(1H-imidazol-4-yl)-1-Propanone

A solution of 4-cyanoimidazole (2 g, 21.4 mmol) in THF (25 ml) was added dropwise to a solution (68.5 mL, 68.5 mmol, 3.2 equivalents) of 1 M ethyl magnesium bromide in THF at 0 to 10° C. under a nitrogen atmosphere. The mixture was stirred at 15 to 25° C. for 4 h. Water (20 ml) and 10% aqueous sulfuric acid solution (45 ml) were successively added dropwise, and the mixture was stirred for 1 h. A 30% aqueous sodium hydroxide solution was added dropwise to adjust the pH to 8. After partitioning, the aqueous layer was extracted with ethyl acetate (15 ml×2). The organic layer was combined, and the mixture was washed successively with saturated aqueous sodium hydrogencarbonate and saturated brine, and concentrated under reduced pressure. The concentration residue was broken up with n-hexane (6 ml), and the crystals were collected by filtration and washed with n-hexane. The crystals were dried in vacuo (40° C.) to give 1-(1H-imidazol-4-yl)-1-propanone (1.68 g, yield 63%). $^1$H-NMR (CDCl$_3$): δ 1.06(3H, t, J=7.4 Hz), 2.86(2H, q, J=7.4 Hz), 7.81(1H, s), 7.84(1H, s)

EXAMPLE 4

Production of 1-(1H-imidazol-4-yl)-1-Butanone

A solution of 4-cyanoimidazole (2 g, 21.4 mmol) in THF (25 ml) was added dropwise to a solution (68.5 mL, 68.5 mmol, 3.2 equivalents) of 1 M n-propyl magnesium bromide in THF at 0 to 10° C. under a nitrogen atmosphere. The mixture was stirred at 15 to 25° C. for 4 h. Water (20 ml) and 10% aqueous sulfuric acid solution (45 ml) were successively added dropwise, and the mixture was stirred at 1 h. A 30% aqueous sodium hydroxide solution was added dropwise to adjust the pH to 8. After partitioning, the aqueous layer was extracted with ethyl acetate (15 ml×2). The organic layer was combined, and the mixture was washed successively with saturated aqueous sodium hydrogencarbonate and saturated brine, and concentrated under reduced pressure. The concentration residue was broken up with n-hexane (12 ml), and the crystals were collected by filtration and washed with n-hexane. The crystals were dried in vacuo (40° C.) to give 1-(1H-imidazol-4-yl)-1-butanone (2.45 g, yield 83%). $^1$H-NMR (CDCl$_3$): δ 0.90 (3H, t, J=7.4 Hz), 1.60 (2H, q, J=7.3 Hz), 3.34 (2H, q, J=7.1 Hz), 7.77 (1H, s), 7.85 (1H, s)

EXAMPLE 5

Production of 4-Cyanoimidazole

Pyridine (150 ml) was added to 4-formylimidazole (50 g, 0.52 mol), and hydroxylamine hydrochloride (40.5 g, 0.585 mol, 1.13 equivalents) was added while stirring the mixture. After stirring for 2 h, acetic anhydride (92.3 ml, 0.978 mol) was added dropwise. The mixture was stirred as it was until the temperature reached room temperature, and 30% aqueous sodium hydroxide solution was added dropwise in a water bath to adjust the pH to 7.9. Ethyl acetate (380 ml) was added for extraction, and the aqueous layer was extracted again with ethyl acetate (250 ml). The organic layer was combined, washed twice with saturated brine and concentrated under reduced pressure. Toluene was added to the concentration residue and the mixture was concentrated under reduced pressure (twice). The concentration residue was broken up with IPE (100 ml), and the crystals were collected by filtration and washed with IPE. The crystals were dried in vacuo (40° C.) to give 4-cyanoimidazole (42.7 9, yield 88.0%). $^1$H-NMR (DMSO-d$_6$): δ 7.91 (1H, s), 8.10 (1H, S)

Industrial Applicability

According to the present invention, a compound having a steroid $C_{17,20}$ lyase inhibitory action can be produced industrially advantageously in a high yield with a less number of steps without using a heavy metal compound.

What is claimed is:
1. A method for producing a compound of the formula:

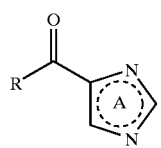

(III)

wherein R is an optionally substituted hydrocarbon group or an optionally substituted heterocyclic group and ring A is an imidazole ring which is optionally substituted further, or a salt thereof, which method comprises reacting a compound of the formula:

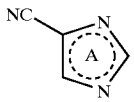 (I)

wherein ring A is as defined above, or a salt thereof, and a compound of the formula:

R—M¹ (II)

wherein $M^1$ is an alkali metal atom or a group of the formula:
—Mg—$Y^1$ where $Y^1$ is a halogen atom, and R is as defined above, or a salt thereof, and bringing the resulting product into contact with an acid.

2. The production method described in claim (1), wherein the ring A of the compounds of the formulas (I) and (III)-is an imidazole ring wherein the 1- or 3-position is optionally substituted.

3. The production method described in claim (1), wherein R is an optionally substituted lower alkyl group, an optionally substituted lower alkenyl group, an optionally substituted cycloalkyl group, an optionally substituted phenyl group or an optionally substituted pyridyl group.

4. The production method described in claim (1), wherein R is a lower alkenyl group, a cycloalkyl group, a phenyl group, a pyridyl group, or a lower alkyl group optionally substituted by a halogen atom.

5. The production method described in claim (1), wherein R is a $C_{1-6}$ alkyl group.

6. The production method described in claim (1), wherein R is an isopropyl group.

7. The production method described in claim (1), wherein the reaction product of a compound of the formula (I) or a salt thereof and a compound of the formula (II) or a salt thereof is brought into contact with a sulfuric acid.

8. The production method described in claim (1), wherein not less than 3 equivalents of the compound of the formula (II) or a salt thereof is used per one equivalent of the compound of the formula (I) or a salt thereof.

9. The production method described in claim (1), wherein the compound of the formula (I) or a salt thereof and the compound of the formula (II) or a salt thereof are reacted in tetrahydrofuran.

10. The production method described in claim (1), wherein the compound of the formula (I) or a salt thereof and the compound of the formula (II) or a salt thereof are reacted in not less than 50 equivalents of a solvent relative to one equivalent of the compound of the formula (I) or a salt thereof.

11. 1-(1H-Imidazol-4-yl)-2-methyl-1-propanone or a salt thereof.

* * * * *